United States Patent
Sprenger et al.

(10) Patent No.: US 11,260,067 B2
(45) Date of Patent: Mar. 1, 2022

(54) METHODS AND COMPOSITIONS FOR DECREASING CONCENTRATIONS OF DETRIMENTAL PROTEOLYTIC METABOLITES, TREATING HEALTH DISORDERS, AND/OR PROMOTING HEALTH BENEFITS IN INFANTS OR YOUNG CHILDREN

(71) Applicant: SOCIETE DES PRODUITS NESTLE S.A., Vevey (CH)

(72) Inventors: Norbert Sprenger, Savigny (CH); Florence Rochat, Montreux (CH); Laurent Favre, Carrouge (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 16/615,903

(22) PCT Filed: May 4, 2018

(86) PCT No.: PCT/EP2018/061490
§ 371 (c)(1),
(2) Date: Nov. 22, 2019

(87) PCT Pub. No.: WO2018/215189
PCT Pub. Date: Nov. 29, 2018

(65) Prior Publication Data
US 2020/0138836 A1 May 7, 2020

(30) Foreign Application Priority Data
May 24, 2017 (EP) .................................. 17172644

(51) Int. Cl.
- A23L 33/00 (2016.01)
- A61K 31/702 (2006.01)
- A61P 1/14 (2006.01)
- A61K 9/00 (2006.01)

(52) U.S. Cl.
CPC .......... *A61K 31/702* (2013.01); *A61K 9/0095* (2013.01); *A61P 1/14* (2018.01)

(58) Field of Classification Search
None
See application file for complete search history.

(56) References Cited

U.S. PATENT DOCUMENTS

| | | | |
|---|---|---|---|
| 10,639,319 B2 * | 5/2020 | Davis | A23L 33/28 |
| 10,940,158 B2 * | 3/2021 | Sangild | A23L 33/21 |
| 2009/0098240 A1 | 4/2009 | Mills et al. | |
| 2009/0305996 A1 | 12/2009 | Beermann et al. | |
| 2013/0236424 A1 | 9/2013 | Sprenger | |
| 2013/0243797 A1 * | 9/2013 | Sprenger | A61K 35/74 424/184.1 |
| 2014/0335065 A1 * | 11/2014 | Davis | A23L 33/28 424/93.44 |
| 2015/0305385 A1 * | 10/2015 | Chichlowski | A61P 1/00 426/2 |
| 2017/0202864 A1 * | 7/2017 | Gallardo | A61K 35/745 |

FOREIGN PATENT DOCUMENTS

| | | | |
|---|---|---|---|
| WO | 2005110121 A1 | | 11/2005 |
| WO | WO 2011/096809 | * | 8/2011 |
| WO | 2016139330 | | 9/2016 |

OTHER PUBLICATIONS

Berger, B. et al. Stool Microbiota in Term Infants Fed Formula Supplemented with Human Milk Oligosaccharides . . . European J of Pediatrics 175(11)1505, Abstract 0942, 2016. (Year: 2016).*
Varquez E. et al. The Human Milk Oligosaccharide 2'-Fucosyllactose Modulates Metabolism of the Infant Intestinal Microbiota. J of Pediatric Gastroenterology and Nutrition 64(Suppl 1)966-967, Abstracts 125 and 126, Apr. 2017. (Year: 2017).*
Tudela et al. "Down-regulation of monocarboxylate transporter 1 (MCT1) gene expression in the colon of piglets is linked to bacterial protein fermentation and pro-inflammatory cytokine-mediated signalling" British Journal of Nutrition, 2015, vol. 113, pp. 610-617.
Wang et al. "Elevated Fecal Short Chain Fatty Acid and Ammonia Concentrations in Children with Autism Spectrum Disorder" Digestive Diseases and Sciences, 2012, vol. 57, No. 8, pp. 2096-2102, XP035091068.
Berggren et al. "Short-chain fatty acid content and pH in caecum of rats given various sources of carbohydrates" Journal of the Science of Food and Agriculture, 1993, vol. 63, pp. 397,406, XP002956474.
Russia Patent Office Communication for Application No. 2019141944, dated Aug. 26, 2021, 14 pages.

* cited by examiner

*Primary Examiner* — Ralph J Gitomer
(74) *Attorney, Agent, or Firm* — K&L Gates LLP

(57) ABSTRACT

The present invention relates to a nutritional composition comprising at least two human milk oligosaccharides, for use to decrease the concentration of detrimental proteolytic metabolites (e.g. branched short chain fatty acids) in the digestive tract in an infant or a young child.

14 Claims, 2 Drawing Sheets

Figure 1:
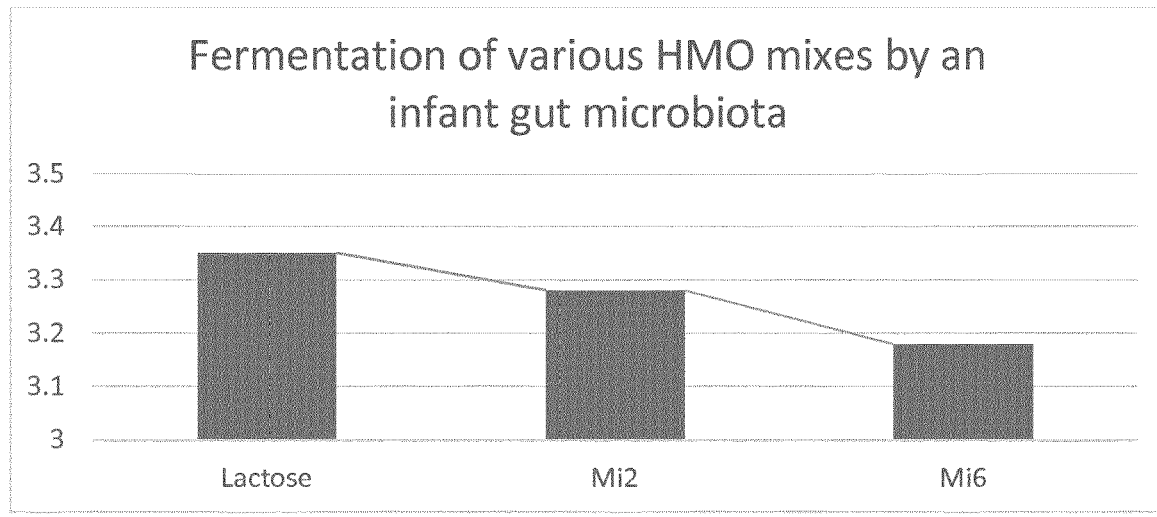

METHODS AND COMPOSITIONS FOR DECREASING CONCENTRATIONS OF DETRIMENTAL PROTEOLYTIC METABOLITES, TREATING HEALTH DISORDERS, AND/OR PROMOTING HEALTH BENEFITS IN INFANTS OR YOUNG CHILDREN

CROSS REFERENCE TO RELATED APPLICATIONS

The present application is a National Stage of International Application No. PCT/EP2018/061490, filed on May 4, 2018, which claims priority to European Patent Application No. 17172644.1, filed on May 24, 2017, the entire contents of which are being incorporated herein by reference

FIELD OF THE INVENTION

This invention relates to nutritional compositions comprising human milk oligosaccharides for use to decrease the concentration of detrimental proteolytic metabolites (e.g. branched short chain fatty acids) in the digestive tract in infants or young children.

BACKGROUND OF THE INVENTION

It has been estimated that the human intestine harbours $10^{13}$ to $10^{14}$ bacterial cells. The microbiota of the human intestine is a complex and very dynamic microbial ecosystem, which is considered to serve numerous important functions for its human host, including protection against pathogens, induction of immune regulatory functions, nutrient processing and metabolic functions. The intestinal microbiota consists of various populations, which are important to preserve human health, and recent research has been able to link imbalances in the intestinal bacterial population to both intestinal and extra-intestinal inflammatory diseases.

Non-digestible carbohydrates that reach the large intestine are used by the indigenous saccharolytic bacteria, which results in production of metabolites such as short-chain fatty acids (SCFAs); mainly acetate, propionate and butyrate. SCFAs exert multiple beneficial effects on human health. Acetate can enhance intestinal defence mediated by epithelial cells and thereby protect the host against assault. Butyrate is mainly metabolised by epithelial cells and has been proposed as the main energy source for colonocytes, and has been reported to regulate the physical and functional integrity of the normal colonic mucosa by altering mucin gene and tight junction expression.

In the large intestine, non-digested dietary compounds as well as secreted endogenous substrates can be fermented by the indigenous bacteria, and the substrate availability is a major driver for bacterial fermentation pathways. Hence, metabolites formed by the gut microbiota are largely determined by the composition of the diet and the pattern of food intake, and it is now clear that the species composition of the colonic microbiota is itself altered by the diet.

Proteins that enter the large intestine non-digested, promote putrefactive fermentation and selective growth of proteolytic bacteria such as members of Fusobacteria, Streptococcaceae, Megasphera, *Selenomonas*, Bacteroidetes and Proteobacteria but also putatively pathogenic species such as *E. coli, Klebsiella* spp., *Campylobacter* spp., *Streptococcus* spp., *C. perfringens* and *C. difficile*. When proteins are utilized by these bacteria, branched short chain fatty acids, ammonia, amines, volatile sulfur compounds and phenolic compounds are produced, some of which are potentially harmful to human health (Pieper et al., Anim Health Res Rev., 2016 17(2):137-147). As they may impair barrier function and promote pro-inflammatory signaling expression in the colonic mucosa.

Ammonia can interfere with the oxidative metabolism of SOFA in colonocytes inducing energy deficiency in the cell and increasing apoptosis and proliferation. Additionally, ammonia and other protein-derived metabolites such as branched SOFA present in the lumen can impair barrier function and promote pro-inflammatory signalling expression in the colonic mucosa, which negatively influence the expression of monocarboxylate transporter 1 (MCT1) (Villodre et al., Brit. J. Nutr., 2015, 113: 610-617). MCT1 is stimulated by butyrate leading to increase butyrate uptake by colonocytes. The inhibition of MCT1 by high concentration of protein-derived metabolites in the intestine can impair the protective effect of butyrate on the colon epithelium and lead to pro-inflammatory conditions in the colon.

Normally, gut-derived ammonia is taken up by the liver and consumed in the urea cycle and passes out of the body in urine. High concentration of ammonia in the blood can cause damage to the liver and affect the central nervous system such as impairing intracerebral synthesis of serotonin and dopamine and producing abnormal neurotransmitters such as octopamine. Elevated levels of detrimental proteolytic metabolites such as ammonia in plasma in patients with acute liver failure and chronic liver disease have been found, and higher concentration of faecal ammonia has been reported in children with autism spectrum disorders (43 mmol/g faeces) compared with control children (32 mmol/g faeces) (Wang L, et al., Dig Dis Sci, 2012, 57, 2096-2102). An important determinant for the degree of proteolytic versus saccharolytic fermentation is the nutrient availability and in particular the ratio of available carbohydrate to nitrogen. The production of protein degradation products can generally be reduced by increasing the amount of fermentable carbohydrate reaching the colon (Vernazza, et al., Prebiotics: Development and Application, Chapter 1, 2006). Hence, selective stimulation of specific saccharolytic intestinal bacteria to promote their growth and metabolic activity, and inhibit the growth of unfavourable bacteria such as proteolytic bacteria could be a helpful approach in shifting the bacterial metabolism from a proteolytic to a saccharolytic metabolism. This leads to reduction of detrimental proteolytic metabolites such as ammonium and branched SOFA, and an increase of beneficial metabolites such as SCFA.

Decreasing such concentration of detrimental proteolytic metabolites such as ammonium and branched SCFA in the digestive tract is therefore in itself a therapeutic solution. It is an attractive target that also provides positive health advantages (by preventing/treating some health disorders and/or by promoting some health benefits).

Mother's milk is recommended for all infants for various reasons. In comparison to formula feeding, breastfeeding has especially been reported to be beneficial for prevention of various disorders like infections (Quigley et al., Breastfeeding and Hospitalization for Diarrheal and Respiratory Infection in the United Kingdom Millennium Cohort Study, 2007; Hanson, Feeding and infant development Breastfeeding and immune function, 2007). Additionally, breast fed infant have a different gut microbiota profile as compared to infants fed with infant formula. Altogether, these factors affect the development of the infant physiology, including metabolism, immunity, protection against infections and overall growth.

However, in some cases breastfeeding is inadequate or unsuccessful for medical reasons or the mother chooses not to breast feed. Infant formula have been developed for these situations. Fortifiers have also been developed to enrich mother's milk or infant formula with specific ingredients.

Prebiotics are non-digestible carbohydrates that contribute to the well-being of their host. They are typically compounds that pass undigested through the upper part of the gastrointestinal tract and stimulate the growth and/or activity of advantageous bacteria such as bifidobacteria that colonize the large bowel by acting as substrate for them or via a cross feeding.

Human milk oligosaccharides (HMOs) are, collectively, the third largest solid constituents in human milk, after lactose and fat. HMOs usually consist of lactose at the reducing end with a carbohydrate core that often contains a fucose or a sialic acid at the non-reducing end. There are over one hundred milk oligosaccharides that have been isolated and characterized in human milk.

Some compositions using HMO ingredients, such as fucosylated oligosaccharides, lacto-N-tetraose, lacto-N-neotetraose and/or sialylated oligosaccharides, have been described for different health purposes, mainly immune purposes.

HMOs are resistant to enzymatic hydrolysis in the small intestine and are thus largely undigested and unabsorbed. The majority of HMOs that reach the colon serve as substrates to shape the gut ecosystem by selectively stimulating the growth of specific saccharolytic bacteria. HMOs are believed to substantially modulate the infant gut microbiota and play a decisive role in the differences in the microbiota of formula-fed and breast-fed infants.

There is a need, therefore, for means, preferably orally or enterally administered means, more preferably dietetic means, for effectively changing the microbiota ecosystem leading to a decrease in the concentration of detrimental proteolytic metabolites such as branched short chain fatty acids in the gastro-intestinal tracts of infants and young children.

There is also a need to deliver branched SCFAs associated health benefits in a manner that is particularly suitable for the young subjects (infants and young children), in a manner that does not involve a classical pharmaceutical intervention as the infants or young children are particularly fragile.

There is a need to deliver such health benefits in the infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

SUMMARY OF THE INVENTION

The present inventors believe that a composition comprising at least two human milk oligosaccharides is particularly efficient to decrease the concentration of detrimental proteolytic metabolites such as branched short chain fatty acids in the digestive tract in an infant or a young child. They have especially demonstrated in in vitro models that the branched SOFA are decreased with mixes of 2 and 6 HMOs. The production of branched SOFA is also decreased with the diversity (or complexity or number of type) of human milk oligosaccharides (more complex the mix of HMOs will be and less branched SOFA will be produced).

As previously mentioned, decreasing branched SOFA production is in itself associated with positive health advantages. A nutritional composition comprising at least two human milk oligosaccharides (e.g. 2 or 6 HMOs) can be used to prevent and/or treat a health disorder, and/or to promote a health benefit in an infant or young child, especially a disorder or benefit influenced by/linked to the branched SOFA concentration.

In a particularly advantageous embodiment, the nutritional composition according to the invention comprises 2'FL and LNnT.

In a particularly advantageous embodiment, the nutritional composition according to the invention comprises 6 (or at least 6) HMOs that are 2'FL, DFL, LNnT, LNT, 3SL and 6SL.

FIGURES

Figure 2:
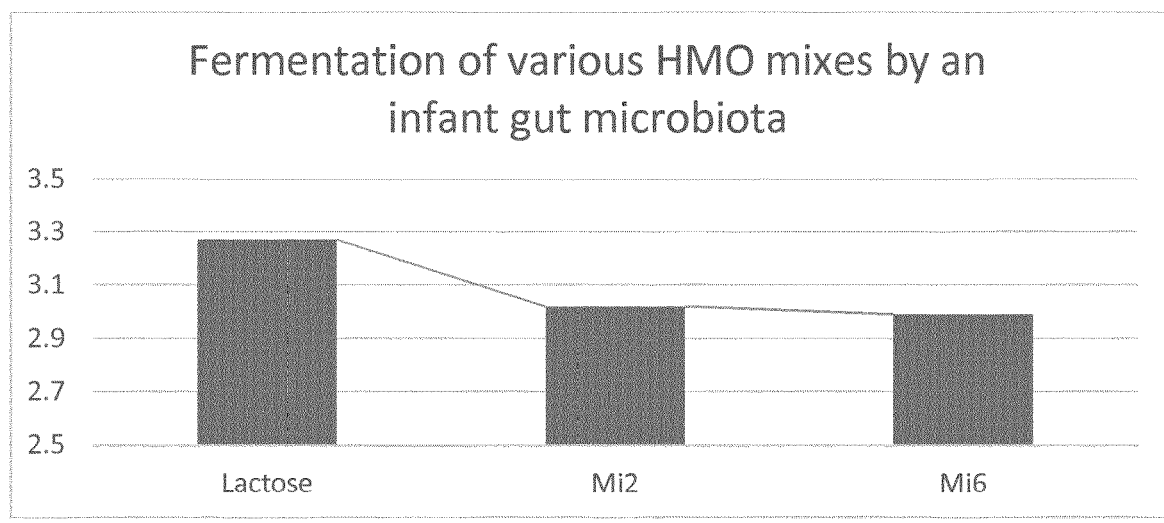
Figure 3:
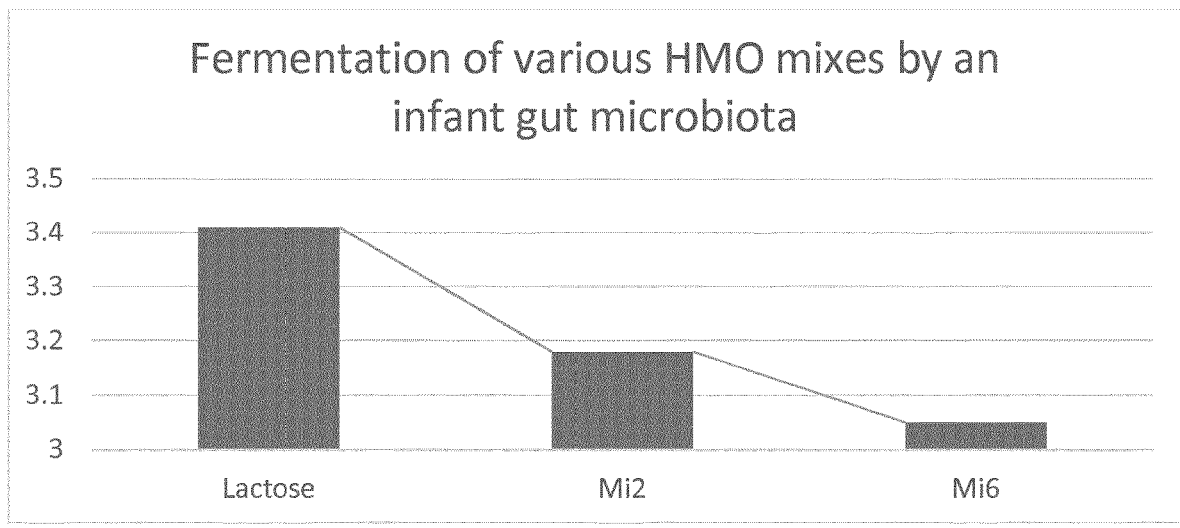
Figure 4:
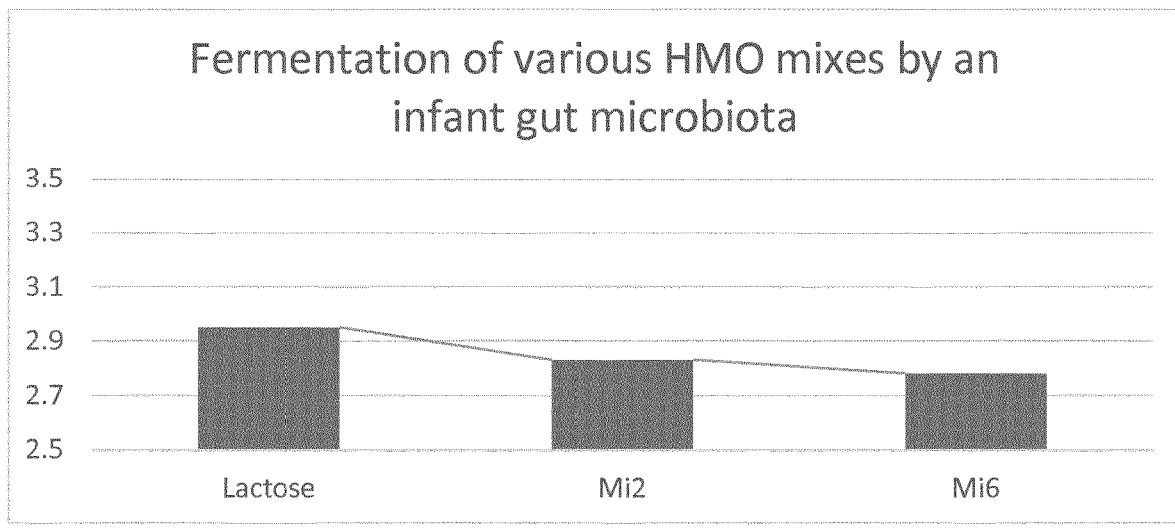

FIG. 1 represents the average branched SCFAs production (mmol/L) in the distal colon associated with the fermentation of three different fiber blends (Mi0, Mi2 and Mi6) after three weeks of treatment.
Mi0: lactose
Mi2: 2'FL, LNnT
Mi6: 2'FL, LNnT, LNT, diFL, 3'SL, 6'SL FIG. 2 represents the average branched SCFAs production (mmol/L) in the proximal colon associated with the fermentation of three different fiber blends (Mi0, Mi2 and Mi6) after three weeks of treatment.
Mi0: lactose
Mi2: 2'FL, LNnT
Mi6: 2'FL, LNnT, LNT, diFL, 3'SL, 6'SL FIG. 3 represents the average branched SCFAs production (mmol/L) in the distal colon associated with the fermentation of three different fiber blends (Mi0, Mi2 and Mi6) during the whole treatment period (n=9).
Mi0: lactose
Mi2: 2'FL, LNnT
Mi6: 2'FL, LNnT, LNT, diFL, 3'SL, 6'SL FIG. 4 represents the average branched SCFAs production (mmol/L) in the proximal colon associated with the fermentation of three different fiber blends (Mi0, Mi2 and Mi6) during the whole treatment period (n=9).
Mi0: lactose
Mi2: 2'FL, LNnT
Mi6: 2'FL, LNnT, LNT, diFL, 3'SL, 6'SL

DETAILED DESCRIPTION OF THE INVENTION

As used herein, the following terms have the following meanings.

The term "infant" means a child under the age of 12 months.

The expression "young child" means a child aged between one and three years, also called toddler.

The expression "child" means a child between three and seven years of age.

An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 36 weeks of gestation.

The expression "nutritional composition" means a composition which nourishes a subject. This nutritional composition is usually to be taken orally or intravenously. It may include a lipid or fat source, a carbohydrate source and/or a protein source. In a particular embodiment the nutritional composition is a ready-to-drink composition such as a ready-to-drink formula.

In a particular embodiment the composition of the present invention is a hypoallergenic nutritional composition. The expression "hypoallergenic nutritional composition" means a nutritional composition which is unlikely to cause allergic reactions.

In a particular embodiment the nutritional composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic nutritional composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The expression "growing-up milk" (or GUM) refers to a milk-base drink generally with added vitamins and minerals, that are intended for young children or children.

The term "fortifier" refers to liquid or solid nutritional compositions suitable for mixing with breast milk or infant formula.

The expression "weaning period" means the period during which the mother's milk is substituted by other food in the diet of an infant or young child.

The expression "health disorder(s)" encompass any health conditions and/or diseases and/or dysfunctions that affect the organism of an individual.

The term "SOFA" means short chain fatty acid(s).

The expressions "branched chain fatty acids", "BCFA", "B-SOFA" and "branched SOFA" can be used interchangeably.

The expression "detrimental proteolytic metabolites" refers to metabolites obtained from the degradation of proteins and amino-acids. They can be branched SCFAs, amines, phenolic compounds or volatile sulfur compounds. In particular it can be ammonia or branched short chain fatty acids. In a preferred embodiment, it refers to branched short chain fatty acids. Examples of branched SOFA are isobutyrate, isovalerate and 2-methyl butyrate. They may be obtained from the conversion of the amino acids valine, leucine and isoleucine obtained from protein breakdown.

The expression "to decrease the concentration of detrimental proteolytic metabolites in the digestive tract" means that the amount of proteolytic metabolites, when measured in the individual in the digestive tract i.e. from the mouth to the rectum (and especially in the intestine, such as in the colon—distal or proximal colon— or large intestine or in a part thereof such as the caecum), is higher in an individual fed with the nutritional composition according to the present invention (i.e. comprising at least 2 HMOs) in comparison with a standard composition (i.e. a nutritional composition not comprising at least 2 HMOs, but for example comprising no HMOs at all). The concentration in the digestive tract may be measured by techniques known by the skilled person such as by Gas-Liquid Chromatography. For example the concentration can be expressed in mg/L for ammonia and in mmol/L for the branched SOFA.

The terms "concentration" and "production" can be used interchangeably in this context.

The "mother's milk" should be understood as the breast milk or the colostrum of the mother.

The term "HMO" or "HMOs" refers to human milk oligosaccharide(s). These carbohydrates are resistant to enzymatic hydrolysis by digestive enzymes (e.g pancreatic and/or brush border), indicating that they may display functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide). Some examples of HMOs are the fucosylated oligosaccharides, the N-acetylated oligosaccharides and/or the sialylated oligosaccharides.

A "fucosylated oligosaccharide" is an oligosaccharide having a fucose residue. It has a neutral nature. Some examples are 2'-FL (2'-fucosyllactose or 2-fucosyllactose or 2FL or 2-FL), 3-FL (3-fucosyllactose), difucosyllactose (DFL or DiFL), lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N-neotetraose) or any combination thereof. Other examples are lacto-N-hexaose, lacto-N-neohexaose, para-lacto-N-hexaose, paralacto-N-neohexaose, lacto-N-octaose, lacto-N-neooctaose, iso-lacto-N-octaose, para-lacto-N-octaose and lacto-N-decaose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

The expression "at least one fucosylated oligosaccharide", "at least one N-acetylated oligosaccharide" and "at least one sialylated oligosaccharide" means "at least one type of fucosylated oligosaccharide", "at least one type of N-acetylated oligosaccharide" and "at least one type of sialylated oligosaccharide".

The expression "at least two fucosylated oligosaccharides", "at least two N-acetylated oligosaccharides" and "at least two sialylated oligosaccharides" means "at least two (different) types of fucosylated oligosaccharides", "at least two (different) types of N-acetylated oligosaccharides" and "at least two (different) types of sialylated oligosaccharides".

A "precursor of HMO" is a key compound that intervenes in the manufacture of HMO, such as sialic acid and/or fucose.

The expressions "galacto-oligosaccharide", "galactooligosaccharide" and "GOS" can be used interchangeably. They refer to an oligosaccharide comprising two or more galactose molecules which has no charge and no N-acetyl residue (i.e. they are neutral oligosaccharide). In a particular embodiment, said two or more galactose molecules are linked by a β-1,2, β-1,3, β-1,4 or β-1,6 linkage. In another embodiment, "galacto-oligosaccharide" and "GOS" also include oligosaccharides comprising one galactose molecule and one glucose molecule (i.e. disaccharides) which are linked by a β-1,2, β-1,3 or β-1,6 linkage.

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or follow-on/follow-up formula or infant cereal product or any other formulation designed for infant nutrition).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995: 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

The present invention therefore refers to a nutritional composition comprising at least two human milk oligosaccharides, for use to decrease the concentration of detrimental proteolytic metabolites in the digestive tract in an infant or a young child.

In a particular embodiment, the human milk oligosaccharides are selected from the list consisting of fucosylated oligosaccharides, N-acetylated oligosaccharides, sialylated oligosaccharides and mixtures thereof.

In a particular embodiment, the nutritional composition comprises at least one human milk oligosaccharide that is a fucosylated oligosaccharide.

In a particular embodiment, the nutritional composition comprises at least one human milk oligosaccharide that is a N-acetylated oligosaccharide.

In a particular embodiment, the nutritional composition comprises at least one human milk oligosaccharide that is a sialylated oligosaccharide.

In a particular embodiment, the nutritional composition comprises at least one human milk oligosaccharide that is a fucosylated oligosaccharide and at least one human milk oligosaccharide that is a N-acetylated oligosaccharide.

In a particular embodiment, the nutritional composition comprises at least one human milk oligosaccharide that is a fucosylated oligosaccharide and at least one human milk oligosaccharide that is a sialylated oligosaccharide.

In a particular embodiment, the nutritional composition comprises at least one human milk oligosaccharide that is a sialylated oligosaccharide and at least one human milk oligosaccharide that is a N-acetylated oligosaccharide.

In a particular embodiment, the nutritional composition comprises at least one fucosylated oligosaccharide and at least one N-acetylated oligosaccharide.

In a particular embodiment, the nutritional composition comprises at least two human milk oligosaccharides that are fucosylated oligosaccharides.

In a particular embodiment, the nutritional composition comprises at least two human milk oligosaccharide that are N-acetylated oligosaccharides.

In a particular embodiment, the nutritional composition comprises at least two human milk oligosaccharides that are sialylated oligosaccharides.

The nutritional composition according to the present invention can comprise (at least) two, three, four, five, six or even more human milk oligosaccharides.

In a particularly advantageous embodiment, it comprises two human milk oligosaccharides, e.g. 2FL and LNnT.

In a particularly advantageous embodiment, it comprises six human milk oligosaccharides, e.g. 2'FL, DFL, LNnT, LNT, 3SL and 6SL.

As previously mentioned, the nutritional composition of the present invention can comprise at least one fucosylated oligosaccharide. There can be one or several types of fucosylated oligosaccharide(s). The fucosylated oligosaccharide(s) can indeed be selected from the list consisting of 2'-fucosyllactose, 3' fucosyllactose, difucosyllactose, lacto-N-fucopentaose (such as lacto-N-fucopentaose I, lacto-N- fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list consisting of 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

In a preferred embodiment, the nutritional composition according to the invention comprises 2'-fucosyllactose (or 2FL, or 2'FL, or 2-FL or 2'-FL) and/or difucosyllactose (DFL or DiFL). It may comprise both 2'FL and DFL. In a particular embodiment, there is no other type of fucosylated oligosaccharides than a combination of 2'-fucosyllactose and difucosyllactose, i.e. the nutritional composition of the invention comprises only 2'-fucosyllactose and difucosyllactose as fucosylated oligosaccharides.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

The nutritional composition of the present invention can also comprise at least one N-acetylated oligosaccharide. There can be one or several types of N-acetylated oligosaccharide. The N-acetylated oligosaccharide(s) can be for example lacto-N-tetraose (LNT), lacto-N-neotetraose (LNnT) or any combination thereof. In some particular embodiments the N-acetylated oligosaccharide is lacto-N-neotetraose (LNnT), para-lacto-N-neohexaose (para-LNnH) or any combination thereof. In some particular embodiments the N-acetylated oligosaccharide is LNnT. In some particular embodiments the N-acetylated oligosaccharide is LNT.

In an embodiment the N-acetylated oligosaccharide is a mixture of LNT and LNnT. In some particular embodiments the composition comprises both LNT and LNnT in a ratio LNT:LNnT between 7:1 to 1:2, or between 5:1 and 1:2, or from 2:1 to 1:1, or from 2:1.2 to 2:1.6. In a particular embodiment the LNT:LNnT ratio is 5:1.

In a particular embodiment, there is no other type of N-acetylated oligosaccharides than a combination of lacto-N-neotetraose (LNnT) and lacto-N-tetraose (LNT), i.e. the nutritional composition of the invention comprises only lacto-N-neotetraose (LNnT) and lacto-N-tetraose (LNT) as N-acetylated oligosaccharides.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety. The N-acetylated oligosaccharide(s) may also be produced by biotechnological means based on microbial fermentation technology.

The nutritional composition of the present invention can also comprise at least one sialylated oligosaccharide. There can be one or several sialylated oligosaccharide(s). The sialylated oligosaccharide(s) can be selected from the group consisting of 3' sialyllactose (3SL), 6' sialyllactose (6SL), and any combination thereof. In an advantageous embodiment the nutritional composition comprises 3SL and 6SL. In some particular embodiments the ratio between 3'-sialyllactose (3SL) and 6'-sialyllactose (6SL) can be in the range between 5:1 and 1:10, or from 3:1 and 1:1, or from 1:1 to 1:10. In a particular embodiment, there is no other type of sialylated oligosaccharides than a combination of 3' sialyllactose (3SL), 6' sialyllactose (6SL), i.e. the nutritional composition of the invention comprises only 3' sialyllactose (3SL) and 6' sialyllactose (6SL) as sialylated oligosaccharides.

The sialylated oligosaccharide(s) may be isolated by chromatographic or filtration technology from a natural source such as animal milks. Alternatively, they may be produced by biotechnological means using specific sialyl-transferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In some aspects of the invention the at least two human milk oligosaccharides of the nutritional composition of the present invention are selected from the list consisting of 2'FL, DFL, LNnT, LNT, 3SL and 6SL.

In a particular embodiment, the nutritional composition according to the present invention comprises 2FL and LNnT.

In a particular embodiment, the nutritional composition according to the present invention comprises six or at least six human milk oligosaccharides that are 2'FL, DFL, LNnT, LNT, 3SL and 6SL.

The present inventors have also surprisingly discovered in their in vitro models that the concentration of detrimental proteolytic metabolites such as branched short chain fatty acids was further decreased with the diversity (or complexity or number of type) of human milk oligosaccharides (comparison was made with HMOs in the same total quantity) i.e. the more there are types of human milk oligosaccharides in the HMOs mix, the lower the concentration of detrimental proteolytic metabolites is (in other words, more complex the mix of HMOs is and less detrimental proteolytic metabolites are produced). Without wishing to be bound by theory, the present inventors believe that the HMOs are acting synergically.

Therefore in an embodiment, the concentration of detrimental proteolytic metabolites (e.g. branched short chain fatty acids) is decreased with the diversity (or complexity or number) of human milk oligosaccharides present in the nutritional composition according to the present invention.

The at least two human milk oligosaccharides present into the nutritional composition of the present invention may be in a total amount of from 0.1 to 10 wt %, or from 0.5 to 7 wt %, or from 0.6 to 1.5 wt % such as from 0.8 to 1.2 wt % of the nutritional composition before reconstitution with water. For reconstituted ready-to-drink formula, the total amount could be from 0.01 to 1%, more preferably 0.05 to 0.7% or 0.1 to 0.5%.

The nutritional composition according to the present invention may also comprise at least another oligosaccharide(s) and/or at least a fiber(s) and/or at least a precursor(s) of human milk oligosaccharide(s). The other oligosaccharide and/or fiber and/or precursor may be selected from the list comprising galacto-oligosaccharides (GOS), fructo-oligosaccharides (FOS), inulin, xylooligosaccharides (XOS), polydextrose, sialic acid, acacia gum, fucose and any combination thereof. They may be in an amount between 0 and 10% by weight of composition.

Suitable commercial products that can be used in addition to the oligosaccharides comprised in the oligosaccharide mixture to prepare the nutritional compositions according to the invention include combinations of FOS with inulin such as the product sold by BENEO under the trademark Orafti, or polydextrose sold by Tate & Lyle under the trademark STA-LITE®.

The composition according to the present invention may optionally also comprise at least one precursor of human milk oligosaccharide. There can be one or several precursor(s). For example the precursor of human milk oligosaccharide is sialic acid, fucose or a mixture thereof. In some particular embodiments the composition comprises sialic acid. In particular examples the composition comprises from 0 to 3 g/L of precursor(s) of human milk oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of human milk oligosaccharide.

The composition according to the invention can contain from 0 to 2.1 g of precursor(s) of human milk oligosaccharide per 100 g of composition on a dry weight basis, e.g. from 0 to 1.5 g or from 0 to 0.8 g or from 0 to 0.15 g of precursor(s) of human milk oligosaccharide per 100 g of composition on a dry weight basis.

The nutritional composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly *Bifidobacteria* and/or *Lactobacilli*.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM 1-1225, *Streptococcus salivarius* DSM 13084 sold by BLIS Technologies Limited of New Zealand under the designation K12, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition according to the invention may contain from 10e3 to 10e12 cfu of probiotic strain, more preferably between 10e7 and 10e12 cfu such as between 10e8 and 1000 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition of the invention can further comprise at least one phage (bacteriophage) or a mixture of phages, preferably directed against pathogenic Streptococci, Haemophilus, Moraxella and Staphylococci.

The nutritional composition according to the invention is preferably a synthetic nutritional composition.

The nutritional composition according to the invention can be for example an infant formula, a starter infant formula, a follow-on or follow-up formula, a baby food, an infant cereal composition, a fortifier such as a human milk fortifier, or a supplement. In some particular embodiments, the nutritional composition of the invention is an infant formula, a fortifier or a supplement that may be intended for the first 4 or 6 months of age. In a preferred embodiment the nutritional composition of the invention is an infant formula.

The present invention also covers a growing-up milk comprising at least two human milk oligosaccharides as defined in the present invention, for use to decrease the concentration of detrimental proteolytic metabolites such as branched short chain fatty acids in the digestive tract in a young child or in a child.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses.

The nutritional composition of the present invention can be in solid (e.g. powder), liquid or gelatinous form.

The nutritional composition according to the invention generally contains a protein source. The protein can be in an amount of from 1.5 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, such as 1.5-1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90. In a particular embodiment a part or all the proteins are amino acids.

In a particular embodiment the nutritional composition according to the invention is a hypoallergenic composition. In another particular embodiment the composition according to the invention is a hypoallergenic nutritional composition.

The nutritional composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s).

The nutritional composition according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The human milk oligosaccharides may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The human milk oligosaccharides may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement.

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in infants or young children. The infants or young children may be born term or preterm. In a particular embodiment the nutritional composition of the invention is for use in infants or young children that were born preterm.

The nutritional composition of the present invention may also be used in an infant or a young child that was born by C-section or that was vaginally delivered.

In a particular embodiment the nutritional composition of the invention is for use in infants or young children born by C-section. These infants or young children may have lower immunity defences and be prone to have inflammation issues (colitis . . . ) because they do not encounter the vaginal mother's microbiota at birth.

In a particular embodiment the nutritional composition of the invention is for use in infants or young children at risk of developing allergies. This may be especially the case for infants or young children born from parents already suffering of allergies.

In some embodiments the nutritional composition according to the invention can be for use before and/or during the weaning period.

The nutritional composition can be administered (or given or fed) at an age and for a period that depends on the possibilities and needs.

When the nutritional composition is used for prevention purposes, it can for example be given immediately after birth of the infants. The nutritional composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4 or 6 months of birth of said infant.

In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on formula.

The present inventors have found that a specific HMOs intervention in in vitro models significantly decreased the branched SOFA production. They have also especially demonstrated that the production is decreased with the diversity (or complexity or number of type) of human milk oligosaccharides.

As previously mentioned, decreasing branched SOFA production is in itself associated with positive health advantages. Therefore a nutritional composition comprising at least two human milk oligosaccharides (e.g. 2 or 6 HMOs) can be used to prevent and/or treat a health disorder, and/or to promote a health benefit in an infant or young child, especially a disorder or benefit influenced by or linked to the branched SOFA production in the digestive tract, especially the colonic production.

Therefore in a particular embodiment, the nutritional composition according to the present invention is used to prevent and/or treat a health disorder, and/or to promote a health benefit in an infant or a young child.

In a specific embodiment, it is used for use to prevent and/or treat a health disorder and/or to promote a health benefit by decreasing the concentration of detrimental proteolytic metabolites such as branched short chain fatty acids in the digestive tract in an infant or a young child.

The health disorder may be for example gut inflammation, gut infections.

The health benefit may be for example gut maturation, gut protection, anti-colonic cancer effects (especially against the colorectal cancer or colon carcinogenesis).

The health advantages targeted in the present invention may be obtained by decreasing the concentration of detrimental proteolytic metabolites such as branched short chain fatty acids in the digestive tract in an infant or a young child, especially the intestinal concentration, such as the colonic concentration (e.g. proximal and/or distal colonic concentration) or the concentration in the caecum. In a particular embodiment the concentration in the digestive tract is measured by Gas-Liquid Chromatography.

In particular, the branched short chain fatty acids that are decreased are selected from the list consisting of isobutyrate, isovalerate, 2-methyl butyrate or any mixtures thereof. In a particular embodiment, with a nutritional composition comprising the at least 2 HMOs the concentration of branched short chain fatty acids in the digestive tract (e.g. in the colon) is decreased by at least 5%, or at least 10% or at least 12% or at least 15% or at least 20% or at least 25% or at least 28% in comparison to the production in the digestive tract obtained with a nutritional composition comprising no human milk oligosaccharide.

Another object of the present invention is a growing-up milk comprising at least two human milk oligosaccharides, for use to decrease the concentration of detrimental proteolytic metabolites such as branched short chain fatty acids in the digestive tract in a young child or in a child.

The different embodiments, details and examples previously described in the specification (e.g. related to the types and amounts of human milk oligosaccharide . . . ) also apply to this other object of the invention.

Another object of the present invention is the use of a nutritional composition comprising at least two human milk oligosaccharides to decrease the concentration of detrimental proteolytic metabolites such as branched short chain fatty acids in the digestive tract (especially the intestinal concentration, such as the colonic concentration or the concentration in the caecum) in an infant or a young child. In a particular embodiment, the use is a non-therapeutic use.

The different embodiments, details and examples previously described in the specification (e.g. related to the types and amounts of human milk oligosaccharide, the nutritional composition, the administration, the targeted population . . . ) also apply to this other object of the invention.

Another object of the present invention is the use of a growing-up milk comprising at least two human milk oligosaccharides to decrease the concentration of detrimental proteolytic metabolites such as branched short chain fatty acids in the digestive tract (especially the intestinal concentration, such as the colonic concentration or the concentration in the caecum) in a young child or in a child. In a particular embodiment, the use is a non-therapeutic use.

The different embodiments, details and examples previously described in the specification (e.g. related to the types and amounts of human milk oligosaccharide . . . ) also apply to this other object of the invention.

Another object of the present invention is the use of at least two human milk oligosaccharides to decrease the concentration of detrimental proteolytic metabolites such as branched short chain fatty acids in the digestive tract (especially the intestinal concentration, such as the colonic concentration or the concentration in the caecum) in an infant or a young child.

The different embodiments, details and examples previously described in the specification (e.g. related to the types and amounts of human milk oligosaccharide, the nutritional composition, the administration, the targeted population . . . ) also apply to this other object of the invention.

Other Objects:

Another object of the present invention is the use of at least two human milk oligosaccharides in the preparation of a nutritional composition for decreasing the concentration of detrimental proteolytic metabolites such as branched short chain fatty acids in the digestive tract in an infant or a young child.

Another object of the present invention is the use of at least two human milk oligosaccharides in the preparation of a growing-up milk for decreasing the concentration of detrimental proteolytic metabolites such as branched short chain fatty acids in a young child or a child.

Another object of the present invention is a pharmaceutical composition comprising at least two human milk oligosaccharides for use in decreasing the concentration of detrimental proteolytic metabolites such as branched short chain fatty acids in the digestive tract in an infant or a young child.

Another object of the present invention refers to a method for decreasing the concentration of detrimental proteolytic metabolites such as branched short chain fatty acids in the digestive tract in an infant or a young child, said method comprising administering to said infant or young child a nutritional composition comprising at least two human milk oligosaccharides.

Another object of the present invention refers to a method for decreasing the concentration of detrimental proteolytic metabolites such as branched short chain fatty acids in the digestive tract in a young child or a child, said method comprising administering to said young child or child a growing-up milk comprising at least two human milk oligosaccharides.

The different embodiments, details and examples previously described in the specification (e.g. related to the types and amounts of human milk oligosaccharide, the nutritional composition, the administration, the targeted population . . . ) also apply to all these other objects. In particular the concentration of detrimental proteolytic metabolites in the digestive tract may be the intestinal concentration, such as the colonic concentration or the concentration in the caecum.

EXAMPLES

The following examples illustrate some specific embodiments of the composition for use according to the present invention. The examples are given solely for the purpose of illustration and are not to be construed as limitations of the present invention, as many variations thereof are possible without departing from the spirit of the invention.

Example 1

An example of the composition of a nutritional composition (e.g. an infant formula) according to the present invention is given in the below table 1. This composition is given by way of illustration only.

TABLE 1 an example of the composition of a nutritional composition (e.g. an infant formula) according to the present invention

| Nutrients | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |

TABLE 1-continued an example of the composition of a nutritional composition
(e.g. an infant formula) according to the present invention

| Nutrients | | per 100 kcal | per litre |
|---|---|---|---|
| α-Linolenic acid (mg) | | 101 | 675 |
| Lactose (g) | | 10.6 | 70.7 |
| Minerals (g) | | 0.37 | 2.5 |
| Na (mg) | | 23 | 150 |
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (μg) | | 8 | 50 |
| Se (μg) | | 2 | 13 |
| Vitamin A (μg RE) | | 105 | 700 |
| Vitamin D (μg) | | 1.5 | 10 |
| Vitamin E (mg TE) | | 0.8 | 5.4 |
| Vitamin K1 (μg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (μg) | | 9 | 60 |
| Pantothenic acid (mg) | | 0.45 | 3 |
| Vitamin B12 (μg) | | 0.3 | 2 |
| Biotin (μg) | | 2.2 | 15 |
| Choline (mg) | | 10 | 67 |
| Fe (mg) | | 1.2 | 8 |
| I (μg) | | 15 | 100 |
| Cu (mg) | | 0.06 | 0.4 |
| Zn (mg) | | 0.75 | 5 |
| Oligosaccharides | 2FL (g) | 0.13 | 0.9 |
| (HMOs) | LNnT (g) | 0.0075 | 0.05 |
| | LNT (g) | 0.04 | 0.25 |
| | DFL (g) | 0.013 | 0.09 |
| | 3SL(g) | 0.014 | 0.1 |
| | 6SL (g) | 0.022 | 0.15 |

Example 2: Long-Term Administration Study

Description of the Study

A known continuous model of the human gastrointestinal tract was used. It is called the Simulator of the Human Intestinal Microbial Ecosystem (SHIME®). This model allows to culture the complex gut microbiota over a longer period under representative conditions for the different intestinal regions. Therefore, the SHIME® does not only allow to obtain detailed information about the fermentation profile of the prebiotic formula, but importantly also about the localization of the intestinal fermentation activity.

The first two reactors are of the fill-and-draw principle to simulate different steps in food uptake and digestion, with peristaltic pumps adding a defined amount of SHIME feed (140 mL 3×/day) and pancreatic and bile liquid (60 mL 3×/day), respectively to the stomach and small intestine compartment and emptying the respective reactors after specified intervals. The last three compartments simulate the large intestine.

The SHIME® experiment for this study consisted of three stages:

Stabilization period: After inoculation of the colon reactors with a fresh faecal sample, a two-week stabilization period allowed the microbial community to differentiate in the different reactors depending on the local environmental conditions. During this period a basic nutritional matrix was provided to the SHIME to support the optimum diversity of the gut microbiota originally present in the faecal inoculum.

Control period: During this two-week reference period, the standard SHIME nutrient matrix was further dosed to the model for a period of 14 days. Analysis of samples in this period allows to determine the baseline microbial community composition and activity in the different reactors, which will be used as a reference for evaluating the treatment effects.

Treatment period: During this three-week period, the SHIME reactor was operated under nominal conditions, but with a diet supplemented with the prebiotic product on top of the normal composition.

Three different fiber blends (Mi0, Mi2 and Mi6) were tested (several doses: the diet supplemented with HMOs was administered 3 times a day at a concentration of 1%):
Mi0: Lactose
Mi2: 2'FL, LNnT
Mi6: 2'FL, LNnT, LNT, diFL, 3'SL, 6'SL Branched SCFAs production were measured three times per week throughout the experiment.

Findings

FIG. 1 represents the average of branched SCFA production (concentration in mmol/L) at the end of the 3 weeks treatment with three different fiber blends (Mi0, Mi2 and Mi6) in the proximal colon. FIG. 2 represents the same data for the distal colon. FIG. 3 represents the average of branched SOFA production (concentration in mmol/L) during three weeks treatment with same blends (Mi0, Mi2 and Mi6) in the proximal colon. FIG. 4 represents the same data for the distal colon.

As it can be seen, the production was decreased with the HMO mixes comprising 2 HMOs (Mi2: 2'FL, LNnT) and 6 HMOs (Mi6: 2'FL, DFL, LNnT, LNT, 3SL and 6SL), in comparison with the branched SOFA production obtained with Lactose (Mi0).

In comparison with the control (no human milk oligosaccharide added), based on the mean of the 3 weeks, the concentration of branched short chain fatty acids in proximal is decreased by at least 15% with Mi2 in comparison to the production obtained with a nutritional composition comprising no human milk oligosaccharide and by 16% with Mi6. In the distal colon the branched SOFA were decreased by 25% with a nutritional composition comprising Mi2 and by 28% with a nutritional composition comprising Mi6. The production of branched SOFA was decreased in both proximal and distal colon for the mix of 2 HMOs (Mi2: 2'FL, LNnT) and even more with 6 HMOs (Mi6: 2'FL, DFL, LNnT, LNT, 3SL and 6SL).

Conclusion:

The production of branched SCFAs was decreased with a HMO mix comprising at least 2 HMOs (e.g. 2 or 6 HMOs).

As previously mentioned, decreasing branched SCFAs production is in itself associated with positive health advantages. Therefore a nutritional composition comprising at least two human milk oligosaccharides (e.g. 6 HMOs) can be used to prevent and/or treat a health disorder, and/or to promote a health benefit in an infant or young child, especially a disorder or benefit influenced by/linked to the branched SCFAs production.

Degradation of proteins and amino-acids results in branched SCFAs. They are recognized to be accompanied by potentially toxic metabolites such as amines, phenolic compounds, and volatile sulfur compounds, which may impair barrier function and promote pro-inflammatory signaling expression in the colonic mucosa.

The invention claimed is:

1. A method of decreasing a concentration of detrimental proteolytic metabolites comprising a branched short chain fatty acid (SCFA) selected from the group consisting of isobutyrate, isovalerate, 2-methyl butyrate, and combinations thereof in a digestive tract in an infant or a young child in need thereof by at least 5% in comparison to a production in the digestive tract obtained with another nutritional composition comprising no human milk oligosaccharides, the method comprising administering to the infant or young child a nutritional composition comprising at least two human milk oligosaccharides in a total amount of from 0.1 to 10 wt % of the nutritional composition and a hydrolyzed protein, the at least two human milk oligosaccharides comprising at least 2'-fucosyllactose (2'FL) and lacto-N-neotetraose (LNnT).

2. The method according to claim 1, wherein the at least two human milk oligosaccharides further comprise sialylated oligosaccharides.

3. The method according to claim 1, wherein the nutritional composition further comprises a fucosylated oligosaccharide selected from the group consisting of 3' fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and combinations thereof.

4. The method according to claim 3, wherein the fucosylated oligosaccharide comprises difucosyllactose (DFL or DiFL).

5. The method according to claim 1, wherein the nutritional composition further comprises lacto-N-tetraose (LNT).

6. The method according to claim 1, wherein the nutritional composition comprises a sialylated oligosaccharide selected from the group consisting of 3' sialyllactose (3SL), 6' sialyllactose (6SL) and combinations thereof.

7. The method according to claim 1, wherein the at least two human milk oligosaccharides further comprise one human milk oligosaccharide selected from the group consisting of DFL, LNT, 3SL, 6SL, and combinations thereof.

8. The method according to claim 1, wherein the nutritional composition comprises at least six human milk oligosaccharides 2'FL, DFL, LNnT, LNT, 3SL and 6SL.

9. The method according to claim 1, wherein the concentration of detrimental proteolytic metabolites in the digestive tract is decreased with the diversity of the at least two human milk oligosaccharides present in the nutritional composition.

10. The method according to claim 1, wherein the at least two human milk oligosaccharides are present in a total amount of from 0.5 to 7 wt % of the nutritional composition.

11. The method according to claim 1, wherein the nutritional composition is in a form selected from the group consisting of an infant formula, a starter infant formula, a follow-on or follow-up infant formula, a baby food, an infant cereal composition, a fortifier and a supplement.

12. A method of treating or reducing a risk of allergies by decreasing a concentration of detrimental proteolytic metabolites comprising a branched short chain fatty acid (SCFA) selected from the group consisting of isobutyrate, isovalerate, 2-methyl butyrate, and combinations thereof in an infant or young child in need thereof by at least 5% in comparison to a production in the digestive tract obtained with another nutritional composition comprising no human milk oligosaccharides, the method comprising administering to the infant or young child a nutritional composition comprising at least two human milk oligosaccharides in a total amount of from 0.1 to 10 wt % of the nutritional composition and a hydrolyzed protein, the at least two human milk oligosaccharides comprising at least 2'FL and LNnT.

13. The method of claim 1, wherein the nutritional composition is a growing-up milk.

14. The method of claim 1, wherein the infant or young child was born by C-section.

* * * * *